United States Patent [19]

Zoller et al.

[11] Patent Number: 5,043,348

[45] Date of Patent: Aug. 27, 1991

[54] PYRROLEALDEHYDES, THEIR PREPARATION AND THEIR USE

[75] Inventors: Gerhard Zoller, Schöneck; Rudi Beyerle, Frankfurt; Ursula Schindler, Morfelden-Walldorf, all of Fed. Rep. of Germany

[73] Assignee: Cassella Aktiengesellschaft, Fed. Rep. of Germany

[21] Appl. No.: 485,277

[22] Filed: Feb. 26, 1990

Related U.S. Application Data

[63] Continuation of Ser. No. 180,302, Apr. 12, 1988, abandoned.

[30] Foreign Application Priority Data

Apr. 24, 1987 [DE] Fed. Rep. of Germany ......... 371725

[51] Int. Cl.$^5$ .................. A61K 31/40; C07D 207/325
[52] U.S. Cl. ..................................... 514/423; 548/530
[58] Field of Search ........................ 548/530; 514/423

[56] References Cited

U.S. PATENT DOCUMENTS

| | | | |
|---|---|---|---|
| 3,334,637 | 8/1967 | Roberts | 548/530 X |
| 3,758,456 | 9/1973 | Fisher et al. | 548/530 X |
| 3,772,287 | 11/1973 | Burrows et al. | 548/530 X |
| 4,002,643 | 1/1977 | Carson | 548/530 |
| 4,008,250 | 2/1977 | Bell et al. | 548/530 X |
| 4,180,660 | 12/1979 | Nudelman et al. | 544/28 |
| 4,701,465 | 10/1987 | Tanaka et al. | 548/530 |
| 4,792,568 | 8/1988 | Auerbach | 514/423 |

FOREIGN PATENT DOCUMENTS

| | | | |
|---|---|---|---|
| 0154353 | 9/1985 | European Pat. Off. | 514/423 |
| 2062984 | 6/1972 | Fed. Rep. of Germany | 548/530 |

OTHER PUBLICATIONS

C.A. 107:7064k, Geiss et al. (1987).

*Primary Examiner*—Joseph Paul Brust
*Attorney, Agent, or Firm*—Perman & Green

[57] ABSTRACT

Pyrrolealdehydes of the formula I

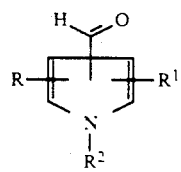 (I)

wherein R and R$^1$ independently of one another denote hydrogen or alkyl with 1 to 4 C atoms, R$^2$ denotes alkyl, which is substituted by acylamino of the formula II

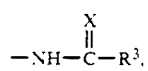 (II)

wherein X stands for an oxygen or sulphur atom and R$^3$ denotes hydrogen, optionally substituted alkyl or alkylamino, cycloalkyl with 5 to 7 C atoms, optionally substituted phenyl, an amino group or an optionally substituted phenylamio group, and pharmaceutically acceptable acid addition salts thereof, and wherein R$^3$ cannot represent hydrogen if R and R$^1$ denote hydrogen and the pyrrole ring is formylated in the 3-position, their preparation and their use.

5 Claims, No Drawings

PYRROLEALDEHYDES, THEIR PREPARATION AND THEIR USE

This is a continuation of copending application Ser. No. 07/180,302, filed on Apr. 12, 1988, now abandoned.

The present invention relates to pyrrolealdehydes of the formula I

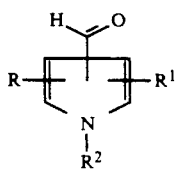

wherein R and $R^1$ independently of one another denote hydrogen or alkyl with 1 to 4 C atoms, $R^2$ denotes alkyl, which is substituted by acylamino of the formula II

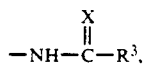

in which: X is an atom selected from the group consisting of oxygen and sulphur, and $R^3$ is selected from the group consisting of:
hydrogen,
alkyl or alkylamino, having 1 to 5 C atoms,
alkyl or alkylamino, having 1 to 5 C atoms and being substituted by —NH$_2$, monoalkylamino with 1 to 4 C atoms, dialkylamino with a total of 2 to 6 C atoms, or phenoxy,
cycloalkyl with 5 to 7 C atoms,
—NH$_2$,
unsubstituted phenyl or phenylamino, and
phenyl or phenylamino which carry up to three substituents in the nucleus selected from the group consisting of chlorine, alkyl with 1 to 2 C atoms, and alkoxy with 1 or 2 C atoms in the alkoxy group;
and pharmaceutically acceptable acid addition salts thereof; provided that $R^3$ is other than hydrogen where R and $R^1$ are hydrogen and the

group is in the 3-position of the pyrrole ring. The invention also relates to a process for the preparation of the compounds of the formula I and their acid addition salts and to their use as pharmacological active compounds.

A phenyl radical $R^3$ and a phenoxy radical bonded as a substituent to an alkyl group $R^2$ or $R^3$ can in turn carry up to three substituents in the nucleus, and in particular an amino group, monoalkylamino with 1 to 4, preferably 1 or 2, C atoms, dialkylamino with a total of 2 to 6, preferably 2 to 4, C atoms, alkanoylamino with 1 to 6, preferably 1 or 2, C atoms, alkyl with 1 to 4, preferably 1 or 2, C atoms, alkoxy with 1 to 4, preferably 1 or 2, C atoms, halogen, preferably fluorine, chlorine or bromine, in particular fluorine or chlorine, hydroxyl, nitro, cyano, carboxyl or alkoxycarbonyl with 1 to 4, preferably 1 or 2, C atoms in the alkoxy group. Possible optional second substituents of the nucleus are: one of the alkyl or alkoxy groups defined above or one of the halogens mentioned above, and possible third substituents are one of the above alkyl or alkoxy groups.

A single substituent can be in the 2-, 3- or 4-position of the phenyl or phenoxy nucleus. In the case of disubstitution, of the possible positions the 2,4-, 3,4- and 3,5-position are preferred. In the case of trisubstitution, the positions 2,3,4, 3,4,5 and 2,4,6 are possible.

Preferred substituents for the phenyl nuclei mentioned are chlorine, alkyl and alkoxy with 1 or 2 C atoms, in particular methyl or methoxy, carboxyl and alkoxycarbonyl with 1 or 2 C atoms in the alkoxy group. In addition to the unsubstituted nuclei, the monosubstituted and disubstituted nuclei which carry an alkoxy radical as a second substituent are furthermore preferred.

As regards the number and position of the substituents in the phenyl nucleus of an optionally substituted phenylamino group $R^3$, the same conditions as for the phenyl and phenoxy radicals described above apply, limited to the substituents which are possible here.

Specific particularly preferred radicals $R^2$ are alkyl radicals with 1 to 3 C atoms, which are substituted by one of the following substituents: formylamino, acetylamino, propionylamino, isopropionylamino, butyrylamino, 4-chlorophenoxyacetylamino, (2-oxopyrrolidin-1-yl)-acetylamino, N,N-dimethylaminoacetylamino, L-thiazolidin-4-yl-carbonylamino, 4-chlorobenzoylamino, 5-oxoperhydro-(1,4)-thiazepin-3-yl-carbonylamino, aminocarbonylamino, 4-chlorophenylaminocarbonylamino, 1-acetyl-L-pyrrolidin-2-ylcarbonylamino, 1-ethyl(pyrrolidin-2-yl), 2-oxopyrrolidin-1-yl, imidazol-4-yl, (2,5-dimethyl-3-formyl)-pyrrol-1-yl or indol-3-yl.

The compounds of the formula I according to the invention can be prepared, for example, by formylation of corresponding pyrroles of the formula III

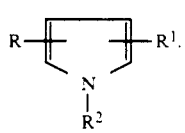

Such pyrroles are described, for example, in DE-OS 3,527,791.2.

Many of the methods described in the literature (see Houben-Weyl, Methoden der Organischen Chemie (Methods of Organic Chemistry), 4th edition, E3, page 16 et seq. (1983)) are suitable as formylating reagents. In specific cases, the Reimer-Tiemann variant by reaction of the pyrroles with chloroform in an alkaline medium is appropriate, but reactions of the pyrroles with 1,1-dihalogenoethers and Friedel-Crafts catalysts (J. Med. Chem. 15, 97 (1972)) or with trialkoxymethanes and trifluoroacetic acid (J. Org. Chem. 43, 283 (1978)) give better yields. In the simplest form, the Vilsmeier-Haack reaction is carried out by reaction of the pyrroles of the formula III with formamides and phosphorus oxychloride to give the compounds according to the invention (Methodicum Chimicum -5, page 234 (1975), J. Org. Chem. 28, 3052 (1963)). Phosphorus oxychloride can be replaced by other compounds, such as oxalyl chloride, thionyl chloride, sulphuryl chloride or cyanuric chloride. The reaction is advantageously carried out in the presence of a solvent, such as dimethylformamide, 1,2-dichloroethane or ethers. Isonitriles in acid solution are also suitable formylating reagents for the compounds according to the invention (Chem. Ber. 94, 298 (1961)).

The pyrroles of the formula III required as precursors can be obtained either by reaction of correspondingly substituted furans with amines of the formula IV $$H_2N-R^2 \quad (IV)$$

(analogously to US 2,655,512) or by reaction of 1,4-dicarbonyl compounds with amines of the formula IV (compare DE-OS 3,527,791.2).

However, the corresponding aldehydes can also be obtained directly, analogously to US 2,655,512, from the furanaldehydes and the corresponding amines.

The reactions are preferably carried out below or at the boiling point of a suitable solvent. If desired, for example if a particularly low-boiling solvent is used, the reaction can also be carried out under pressure above the boiling point of the reaction mixture.

Suitable solvents are, for example, alcohols, in particular those with 1 to 6 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8 C atoms in the molecule, such as, for example, diethyl ether, methyl ethyl ether, di-n-propyl ether, diisopropyl ether, methyl n-butyl ether, ethyl propyl ether, dibutyl ether, tetrahydrofuran, 1,4-dioxane, 1,2-dimethoxyethane and bis-β-methoxyethyl ether; polyethers, such as, for example, polyethylene glycols with a molecular weight of up to about 600; oligoethylene glycol dimethyl ethers, such as, for example, pentaglyme; aliphatic carboxylic acids, in particular formic and acetic acid; glycols and partly etherified glycols, such as, for example, ethylene glycol, propylene glycol, trimethylene glycol, ethylene glycol monomethyl ether, ethylene glycol monoethyl ether and diethylene glycol monoethyl ether; aliphatic hydrocarbons, such as, for example, low- and high-boiling petroleum ether; aromatic hydrocarbons, such as, for example, benzene, toluene or o-, m- or p-xylene; halogenated aliphatic or aromatic hydrocarbons, such as, for example, methylene chloride, chloroform, carbon tetrachloride, chlorobenzene and dichlorobenzene; nitriles, such as, for example, acetonitrile; amides, such as, for example, dimethylformamide and N-methyl-pyrrolidone; hexamethylphosphoric acid triamide; sulphoxides, such as, for example, dimethylsulphoxide; and water. Mixtures of various solvents can also be used.

The amine of the formula IV can also be used in the form of an acid addition salt. The mixtures are worked up by customary methods. If appropriate, the reaction can also be carried out in the presence of a base or a base mixture. Suitable bases are, for example, tertiary aliphatic amines, such as, for example, triethylamine, tri-n-propylamine and tri-iso-propylamine, and furthermore pyridine, as well as alkali metal carbonates and bicarbonates.

By splitting off the acyl radical from compounds of the formula I according to the invention in which R² is an alkyl radical substituted by the group of the formula II

the corresponding compounds in which the alkyl radical R² is substituted by a primary amino group can be obtained. The splitting off is carried out hydrolytically in a manner which is known per se. For this, the compounds are treated with water or a water-containing organic medium in the presence of molar amounts of a base. The treatment time depends on the temperature chosen. The treatment can be carried out at room temperature or, in order to accelerate the hydrolysis, at elevated temperature, advantageously up to the reflux temperature of the liquid hydrolysis medium.

The nature of the base to be added is in principle irrelevant. These reagents should merely bring about a sufficiently high OH⁻ concentration and permit easy working up of the mixtures. These agents can therefore be chosen in a known manner.

To prepare the compounds of the formula I according to the invention in which R² is an alkyl radical which is substituted by an acylamino group of the formula II

it is also possible for aminoalkylpyrrolealdehydes of the formula V

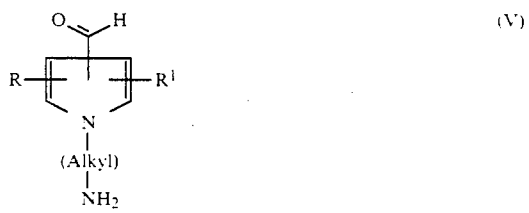

to be acylated with reactive carboxylic acid derivatives derived from carboxylic acids of the formula VI $$R^3-COOH \quad (VI)$$

wherein R³ has the abovementioned meaning, or alternatively with an alkali metal cyanate or thiocyanate or with isocyanates or isothiocyanates of the formula VII $$R^5-NCX \quad (VII)$$

wherein X is oxygen or sulphur and R⁵ denotes phenyl or alkyl, which is optionally substituted in the manner specified above.

Suitable reactive carboxylic acid derivatives are carboxylic acid esters, carboxylic acid anhydrides, carboxylic acid chlorides or carboxylic acids which are activated in situ, such as, for example, dicyclohexylcarbodiimide (Houben Weyl 8, 522); oxalylchloride (GB 2,139,225); N,N-carbonyldiimidazole (J. Med. chem. 1982; 620, Synthesis 1982, 833; and Chem. Pharm. Bull. 32, 5044 (1984)); N,N'-carbonyldiazoles (Bull. Chem. Soc. Jap. 57, 3597 (1984)); di-(2-pyridyl) carbonate (Tetrahedron Lett. 25, 4943 (1983)); chloroformic acid esters (Tetrahedron Lett. 24, 3365 (1983)); diphosphorus tetraiodide (Chem. Lett. 1983, 449); dialkyl disulphites (Indian J. Chem. 21. 259 (1982)); methylethylphosphinic anhydride or other reactive agents.

If isocyanates or isothiocyanates of the formulae R⁵—NCO and R⁵—NCS are used as acylating agents, those pyrrole derivatives according to the invention in which R² is an alkyl radical substituted by the group —HN—CO—NH—R⁵ or —NH—CS—NH—R⁵ are obtained. Reaction of the amines of the formula V with alkali metal cyanates or thiocyanates gives compounds according to the invention in which $R^2$ is an alkyl radical substituted by the group —NH—CO—NH$_2$ or —NH—CS—NH$_2$.

The reactions are advantageously carried out in the liquid phase, the presence of an inert solvent being advantageous.

If enantiomerically pure carboxylic acid derivatives or amines of the formula V are employed, the compounds of the formula I according to the invention can also be obtained as enantiomerically pure compounds.

Another possibility for the preparation of the compounds according to the invention is based on 2,5-dialkoxy-tetrahydrofuranaldehydes of the formula VIII, which can be reacted with amines of the formula IV directly, under acid catalysis, to give correspondingly substituted pyrrolealdehydes of the formula I (compare Synthesis 1973, 422).

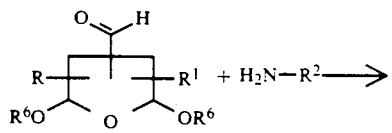

(VIII)    (IV)

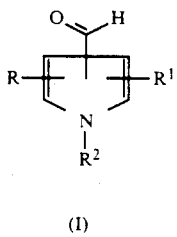

(I)

$R^6$ denotes lower alkyl with 1 to 4 C atoms.

Compounds of the formula III can also be synthesized analogously to this method (Synthesis 1981, page 482), and can then be formylated by the processes described above.

If the compounds of the formula I according to the invention contain basic radicals, they form acid addition salts with inorganic or organic acids. Inorganic and organic acids are suitable for the formation of such acid addition salts. Examples of suitable acids are: hydrochloric acid, hydrobromic acid, naphthalenedisulphonic acids, in particular naphthalene-1,5-disulphonic acid, and phosphoric, nitric, sulphuric, oxalic, lactic, tartaric, acetic, salicylic, benzoic, formic, propionic, pivalic, diethylacetic, malonic, succinic, pimelic, fumaric, maleic, malic, sulphamic, phenylpropionic, gluconic, ascorbic, nicotinic, isonicotinic, methanesulphonic, p-toluenesulphonic, citric or adipic acid. Pharmacologically acceptable acid addition salts are preferred. The acid addition salts are prepared in the customary manner by combining the components, advantageously in a suitable solvent or diluent. In the synthesis of the compounds of the formula I, the acid addition salts can initially be obtained in the course of working up. If desired, the free compounds of the general formula I can be obtained from the acid addition salts in a known manner, for example by dissolving or suspending in water and rendering the solution or suspension alkaline, for example with sodium hydroxide solution, followed by isolation.

The compounds of the formula I according to the invention and their pharmaceutically acceptable acid addition salts have useful pharmacological properties. They have an action on the central nervous system, for example they exhibit encephalotropic and nootropic actions, and are used for the treatment of diseases of cerebral functions, such as cerebral insufficiency, cerebral ageing processes and reduced memory capacity, such as arise with Alzheimer's disease or multi-infarction dementia or with reduced learning performance. Surprisingly, they are considerably superior to the compounds known hitherto with the same type of action. They exhibit an excellent efficacy in the most diverse tests, such as, for example, in prolonging survival time under sodium nitrite hypoxia in accordance with the method of Gibsen and Bless (J. Neurochemistry 27, (1976)), and in improving nitrogen-induced hypoxia tolerance, experimental animals being respirated with pure nitrogen, following premedication with the preparations investigated, and the increase in the period between the start of respiration and electrical neutrality of the electroencephalogram as well as the lethality being measured.

The products according to the invention also have a very good action in tests targeted directly at measuring learning and memory capacity, such as; for example, the known "avoidance" tests.

Testing in the tests mentioned and in a number of other tests, such as, for example, the γ-butyrolactone test, shows that low doses of the compounds according to the invention surprisingly have a particularly favourable action profile which is not present in known preparations of this form, coupled with a low toxicity.

The compounds of the formula I and their physiologically tolerated salts thus represent an enrichment of pharmacy.

It has furthermore been found that the already known compounds of the formula I in which alkyl $R^2$ is substituted by a carboxylic acid grouping and R and/or $R^1$ denote hydrogen (see, for example, V. Carelli et al., Ann.Chim. Appl. 53, 309 (1963); A. Nudelman et al., J. Med. Chem. 21, 962 (1978); and K. Olsson et al., Acta Chem. Scand. Ser.B., 33, 125 (1979)) and the already known compounds of the formula I in which $R^3$ and R and $R^1$ represent hydrogen and the pyrrole ring is formylated in the 3-position (DE-A 3,531,504) also have the same pharmacological properties acting on the central nervous system. These compounds can also be prepared by the synthesis methods described above.

The compounds of the formula I according to the invention and the abovementioned compounds and their pharmaceutically acceptable acid addition salts can therefore be used on humans as medicines, for example in combating or preventing diseases caused by a restriction in cerebral function and in the treatment and prevention of cerebral ageing processes.

The compounds of the formula I and the abovementioned compounds and their pharmaceutically acceptable acid addition salts can be administered as medicines by themselves, as mixtures with one another or in the form of pharmaceutical formulations which allow enteral or parenteral use and contain, as the active constituent, an effective dose of at least one compound of the formula I or of the abovementioned compounds or of an acid addition salt thereof, alongside customary pharmaceutically acceptable excipients and additives. The formulations usually contain about 0.5 to 90% by weight of the therapeutically active compound.

The medicines can be administered orally, for example in the form of pills, tablets, lacquered tablets, coated tablets, granules, hard and soft gelatine capsules, solutions, syrups, emulsions or suspensions or aerosol mixtures. However, the administration can also be rectal, for example in the form of suppositories, or parenteral, for example in the form of injection solutions, or percutaneous, for example in the form of ointments or tinctures.

The pharmaceutical preparations are prepared in a manner which is known per se, pharmaceutically inert inorganic or organic excipients being used. Lactose, maize starch or derivatives thereof, talc, stearic acid or salts thereof, and the like can be used, for example, to prepare pills, tablets, coated tablets and hard gelatine capsules. Excipients for soft gelatine capsules and suppositories are, for example, fats, waxes, semisolid and liquid polyols, natural or hardened oils and the like. Suitable excipients for the preparation of solutions and syrups are, for example, water, sucrose, invert sugar, glucose, polyols and the like. Suitable excipients for the preparation of injection solutions are, for example, water, alcohols, glycerol, polyols, vegetable oils and the like.

In addition to the active compounds and excipients, the pharmaceutical preparations can also contain additives, such as, for example, fillers, extenders, disintegrating agents, binders, lubricants, wetting agents, stabilizers, emulsifiers, preservatives, sweeteners, colouring agents, flavouring agents, aromatizing agents, thickeners, diluents or buffer substances, and furthermore solvents or solubilizing agents or agents for achieving a depot effect, as well as salts for modifying the osmotic pressure, coating agents or antioxidants. They can also contain two or more compounds of the formula I or their pharmacologically acceptable acid addition salts and also one or more other therapeutically active substances.

Such other therapeutically active substances are, for example, circulation-promoting agents, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetyldigoxin, metildigoxin and lanato-glycosides; coronary dilators, such as carbocromen, dipyridamol, nifedipine and perhexiline, antianginal compounds, such as isosorbide dinitrate, isosorbide mononitrate, glycerol nitrate, molsidomine and verapamil, and $\beta$-blockers, such as propranolol, oxprenolol, atenolol, metoprolol and penbutolol. The compounds can moreover be combined with other substances with a nootropic action, such as, for example, piracetam, or substances with an action on the central nervous system, such as pirlindole, sulpiride and the like.

The dosage can be varied within wide limits and is to be adapted to suit the individual circumstances in each individual case. In general, a daily dose of about 0.1 to 1 mg/kg, preferably 0.3 to 0.5 mg/kg of body weight is appropriate with oral administration to achieve effective results, and with intravenous administration the daily dose is in general about 0.01 to 0.3 mg/kg, preferably 0.05 to 0.1 mg/kg of body weight. The daily dose is usually divided into several, for example 2, 3 or 4, part administrations, especially where relatively large amounts are administered. If appropriate, depending on the individual behaviour, it may be necessary to deviate upwards or downwards from the stated daily dose.

Pharmaceutical preparations usually contain 0.1 to 50 mg, preferably 0.5 to 10 mg, of active compound of the formula I or of a pharmacologically acceptable salt thereof per dose.

The following Examples 1 to 11 relate to the preparation of the compounds of the formula I, and Examples A to H relate to the preparation of formulations of the compounds of the formula I.

EXAMPLE 1

1-(2-Acetylaminoethyl)-2,5-dimethylpyrrole-3-aldehyde 15.5 ml (0.166 mol) of phosphorus oxychloride are slowly added dropwise to 13 ml (0.168 mol) of anhydrous dimethylformamide at 0° C. The mixture is stirred at 10° C. for 15 minutes, 70 ml of 1,2-dichloroethane are added and 29.4 g (0.163 mol) of 1-(2-acetylaminoethyl)-2,5-dimethylpyrrole in 25 ml of 1,2-dichloroethane are then added dropwise at 5° C. The mixture is stirred at room temperature for 6 hours, 79.5 g (0.97 mol) of sodium acetate in 130 ml of water are added, the mixture is heated under reflux for 15 minutes, the phases are separated and the organic phase is concentrated.

The residue is boiled up with toluene and the product obtained is filtered off and recrystallized from ethyl acetate. Yield: 17.7 g (52% of theory)

Melting point: 119°–120° C.

Elemental analysis: $C_{11}H_{16}N_2O_2$ (208.26).

Calculated: C 63.4 H 7.7 N 13.5 O 15

Found: C 63.3 H 7.7 N 13.5 O 15.4

The following can be prepared analogously to Example 1:

EXAMPLE 2

Starting from 1-(2-acetylaminoethyl)-5-methyl-pyrrole: 1-(2-acetylaminoethyl)-5-methyl-pyrrole-2-aldehyde Melting point: 87°–90° C.

EXAMPLE 3

Starting from 1-(2-(4(5)-imidazolyl)-ethyl)-2,5-dimethylpyrrole:

1-(2-(4(5)-imidazolyl)-ethyl)-2,5-dimethyl-pyrrole-3-aldehyde

Melting point: 157°–160° C.

EXAMPLE 4

Starting from 1-(3-acetylaminopropyl)-2,5-dimethylpyrrole:

1-(3-acetylaminopropyl)-2,5-dimethyl-pyrrole-3-aldehyde

EXAMPLE 5

Starting from 1-(2-butyrylaminoethyl)-2,5-dimethylpyrrole:

1-(2-butyrylaminoethyl)-2,5-dimethyl-pyrrole-3-aldehyde

Melting point: 75°–76° C.

EXAMPLE 6

Starting from 1-(2-acetylaminoethyl)-pyrrole:
1-(2-acetylaminoethyl)-pyrrole-2-aldehyde
Melting point: 60°–61° C.

EXAMPLE 7

Starting from 1-(2-(pyrrolidin-2-on-1-yl)ethyl-2,5-dimethyl-pyrrole:

1-(2-(pyrrolidin-2-on-1-yl)ethyl)-2,5-dimethyl-pyrrole-3-aldehyde

Melting point: 122°–124.5° C.

EXAMPLE 8

1,2-Di-(2,5-dimethyl-3-formyl-pyrrol-1-yl)-ethane 8.7 ml (0.093 mol) of phosphorus oxychloride are slowly added dropwise to 7.2 ml (0.093 mol) of anhydrous dimethylformamide at 0° C. The mixture is stirred at 10° C. for 15 minutes, 10 ml of 1,2-dichloroethane are added, and 10 g (0.046 mol) of 1,2-di-(2,5-dimethyl-pyrrol-1-yl)-ethane in 40 ml of 1,2-dichloroethane are added dropwise at 5° C. After a reaction time of 15 hours at room temperature, 100 g of sodium acetate in 150 ml of water are added, the mixture is heated under reflux for 5 minutes, methylene chloride is added, the phases are separated, the organic phase is concentrated and the residue is recrystallized from isopropanol.

Yield: 5.5 g (44% of theory).
Melting point: 225°–227° C.
Elemental analysis: $C_{16}H_{20}N_2O_2$ (272.35).
Calculated: C 70.6, H 7.4, N 10.3, O 11.7.
Found: C 71.1, H 7.7, N 10.3, O 11.5.

EXAMPLE 9

2,5-Dimethyl-1-(methoxycarbonylmethyl)-pyrrole-3-aldehyde 17 ml (0.18 mol) of phosphorus oxychloride, 14 ml (0.18 mol) of anhydrous dimethylformamide and 30 g (0.18 mol) of methyl (2,5-dimethyl-pyrrol-1-yl)-acetate are reacted in 140 ml of 1,2-dichloroethane as described above.

Yield: 16.2 g (46% of theory).
Melting point: 83°–85° C.
Elemental analysis: $C_{10}H_{13}NO_3$ (195.22).
Calculated: C 61.5, H 6.7, N 7.2, O 24.6.
Found: C 61.8, H 6.9, N 7.1, O 24.8.

EXAMPLE 10

1-(2-Acetylaminoethyl)-pyrrole-3-aldehyde 8.5 g (0.053 mol) of 2,5-dimethoxytetrahydrofuran-3-aldehyde and 5.4 g (0.053 mol) of 2-(acetylamino)-ethylamine are stirred at 60° C. for 1 hour. After addition of 0.05 g of p-toluenesulphonic acid hydrate, the mixture is stirred at 80° C. for 90 minutes and cooled, sodium bicarbonate solution is added and the mixture is extracted with methylene chloride and then with pentanol. The organic phases are concentrated and chromatographed over a silica gel column with methylene chloride/methanol =95:5 as the mobile phase. The product isolated is crystallized from ethyl acetate/ligroin.

Yield: 2.3 g (24% of theory)
Melting point: 58°–60° C.
Elemental analysis: $C_9H_{12}N_2O_2$ (180.21)
Calculated: C 60.0 H 6.7 N 15.5 O 17.8
Found: C 59.5 H 6.8 N 15.3 O 18.3

EXAMPLE 11

1-(2-Dimethylaminoethyl)-2,5-dimethylpyrrole-3'-aldehyde tartrate 9.8 ml (0.107 mol) of phosphorus oxychloride are added dropwise to 8.2 ml (0.106 mol) of anhydrous dimethylformamide at 0° C. The mixture is stirred at 10° C. for 15 minutes, 20 ml of 1,2-dichloroethane are added, and 17.1 g (0.103 mol) of 2,5-dimethyl-1-(2-dimethylamino)-pyrrole in 60 ml of 1,2-dichloroethane are added dropwise at 5° C. The mixture is stirred at room temperature for 20 hours, 50 g of sodium acetate in 100 ml of water are added, the mixture is heated under reflux for 15 minutes, cooled and extracted with methylene chloride and the extract is concentrated. After chromatography over a silica gel column (mobile phase:methylene chloride:methanol=99:1 to 96:11), the product is dissolved in isopropanol, tartaric acid is added and the precipitate is filtered off with suction and dried.

Yield: 10.1 g (28% of theory).
Melting point: 171°–173° C.
Elemental analysis: $C_{15}H_{24}N_2O_7$ (344.36).
Calculated: C 52.3, H 7.0, N 8.1, O 32.5.
Found: C 52.1, H 6.7, N 8.0, O 32.5.

EXAMPLE 12

1-(Aminocarbonylmethyl)-2,5-dimethylpyrrole-3-aldehyde

Melting point: 217°–220° C.

EXAMPLE 13

1-(2-Benzoylaminoethyl)-2,5-dimethyl-pyrrole-3-aldehyde

Melting point: 119°–120° C.

EXAMPLE 14

1-(2-(Indol-3-yl)-ethyl)-2,5-dimethyl-pyrrole-3-aldehyde

Melting point: 151°–153° C.

EXAMPLE A

Emulations with 3 mg of active compound per 5 ml can be prepared in accordance with the following recipe:

| Active compound | 0.06 g |
|---|---|
| Neutral oil | q.s. |
| Sodium carboxymethylcellulose | 0.6 g |
| Polyoxyethylene stearate | q.s. |
| Pure glycerol | 0.2 to 2 g |
| Aroma substances | q.s. |
| Water (demineralized or distilled) | to 100 ml |

EXAMPLE B

Tablets can be prepared in accordance with the following recipe:

| Active compound | 2 mg |
|---|---|
| Lactose | 60 mg |
| Maize starch | 30 mg |
| Soluble starch | 4 mg |
| Magnesium stearate | 4 mg |
| | 100 mg |

EXAMPLE C

The following composition is suitable for the preparation of soft gelatine capsules with 5 mg of active compound per capsule:

| Active compound | 5 mg |
|---|---|
| Mixture of triglycerides from coconut oil | 150 mg |

-continued

| Capsule contents | 155 mg |
|---|---|

EXAMPLE D

The following formulation is suitable for the preparation of coated tablets:

| Active compound | 3 mg |
|---|---|
| Maize starch | 100 mg |
| Lactose | 55 mg |
| Secondary calcium phosphate | 30 mg |
| Soluble starch | 3 mg |
| Magnesium stearate | 5 mg |
| Colloidal silicic acid | 4 mg |
| | 200 mg |

EXAMPLE E

Coated tablets containing an active compound according to the invention and another therapeutically active substance:

| Active compound | 6 mg |
|---|---|
| Propranolol | 40 mg |
| Lactose | 90 mg |
| Maize starch | 90 mg |
| Secondary calcium phosphate | 34 mg |
| Soluble starch | 3 mg |
| Magnesium stearate | 3 mg |
| Colloidal silicic acid | 4 mg |
| | 270 mg |

EXAMPLE F

Coated tablets containing an active compound according to the invention and another therapeutically active substance:

| Active compound | 5 mg |
|---|---|
| Pirlindole | 5 mg |
| Lactose | 60 mg |
| Maize starch | 90 mg |
| Secondary calcium phosphate | 30 mg |
| Soluble starch | 3 mg |
| Magnesium stearate | 3 mg |
| Colloidal silicic acid | 4 mg |
| | 200 mg |

EXAMPLE G

Capsules containing an active compound according to the invention and another therapeutically active substance:

| Active compound | 5 mg |
|---|---|
| Nicergoline | 5 mg |
| Maize starch | 185 mg |
| | 195 mg |

EXAMPLE H

Injection solutions with 1 mg of active compound per ml can be prepared in accordance with the following recipe:

| Active compound | 1.0 mg |
|---|---|
| Polyethylene glycol 400 | 0.3 mg |
| Sodium chloride | 2.7 mg |
| Water for injection purposes to | 1 ml |

The following results, for example, were found during pharmacological testing:

Nitrite Hypoxia in Mice

In this test, cerebral hypoxia leading to massive disturbances in the behaviour of the animals is generated in mice with $NaNO_2$ (175 mg/kg subcutaneously) in accordance with the method of Gibson and Blass (J. Neurochem. 27, 37 (1976)). It is ascertained whether the ability to hold onto a rotating rod is influenced by premedication with the test substance. The compounds according to the invention are administered here in a dose of 3 mg/kg perorally. The results are shown in the following table.

TABLE

Percentage reversal of disturbance in the ability to hold after administration of 175 mg/kg of $NaNO_2$ subcutaneously and premedication with the compounds of the formula

| Compound according to Example | | Percentage reversal of the hypoxia effect |
|---|---|---|
| No. 1 | | 67 |
| 4 | | 46 |
| 5 | | 23 |
| 6 | | 66 |
| 7 | | 18 |
| 8 | | 36 |
| 9 | | 72 |
| 10 | | 73 |
| 11 | | 31 |
| 12 | | 44 |
| Piracetam (comparison with | 10 mg/kg | 19 |
| | 100 mg/kg | 58 |

"Passive avoidance"

The test apparatus is a light-dark box with a grid floor which can be electrified in the dark part.

55 minutes after administration of a control or preparation injection, inexperienced male mice are treated with scopolamine hydrobromide (3 mg/kg intraperitoneally). 5 minutes later, the mice are placed in the light section of the box. After changing over to the dark section of the box, they are given an unpleasant electric shock to the feet. After 24 hours, each mouse is again placed in the light section of the test apparatus and the residence time (maximum 180 seconds) is measured. The animals treated with an active dose of a preparation and scopolamine show a long residence time, as do the animals which have not been treated with scopolamine, whereas those treated with a control injection and scopolamine show a short residence time. The compounds according to the invention are administered here in a dose of 3 to 30 mg/kg p.o. The results are shown in the following table. In this test, the known compound piracetam achieves a percentage attenuation of 100% in a dose of 60 mg/kg perorally.

TABLE

Percentage attenuation of the scopolamine-induced amnesia, detectable by an increase in the time taken to step into the dark part of the passive avoidance test chamber.

| Compound according to Example No. | Dose (mg/kg) p.o. | Percentage Decrease |
| --- | --- | --- |
| 1 | 3 | 219 |
| 4 | 30 | 92 |
| 5 | 30 | 96 |
| 6 | 10 | 63 |
| 8 | 10 | 297 |
| 9 | 3 | 108 |
| 10 | 3 | 126 |
| 11 | 30 | 128 |
| 12 | 30 | 146 |
| 13 | 30 | 124 |
| 14 | 30 | 98 |
| Piracetam (Comparison) | 30 | 18 |

We claim:

1. Pyrrolaldehydes of the formula I

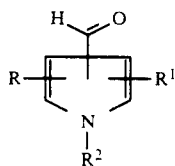

wherein R and $R^1$ independently of one another are selected from the group consisting of hydrogen and alkyl with 1 to 4 C atoms; $R^2$ is alkyl with 1 to 3 atoms, which is substituted by an acylamino group of the formula:

$$-NH-\overset{\overset{X}{\|}}{C}-R^3.$$

in which: X is an atom selected form the group consisting of oxygen and sulphur, and $R^3$ is selected from the group consisting of:
hydrogen,
alkyl of alkylamino, having 1 to 5 C atoms,
alkyl or alkylamino, having 1 to 5 C atoms and being substituted by $-NH_2$, monoalkylamino with 1 to 4 C atoms, dialkylamino with a total of 2 to 6 C atoms, or phenoxy,
cycloalkyl with 5 to 7 C atoms,
$-NH_2$,
unsubstituted phenyl or phenylamino, and
phenyl or phenylamino which carry up to three substituents in the nucleus selected from the group consisting of chlorine, alkyl with 1 to 2 C atoms alkoxy with 1 or 2 C atoms, carboxyl, and alkoxycarbonyl with 1 or 2 C atoms in the alkoxy group; and the pharmaceutically acceptable acid addition salts thereof, provided that $R^3$ is other than hydrogen where R and $R^1$ are hydrogen and the pyrrole ring is formylated in the 3-position.

2. 1-(2-Acetylaminoethyl)-2,5-dimethylpyrrole-3-aldehyde.

3. A pharmaceutical formulation which exhibits encephalotropic and nootropic actions when administered to a host in need thereof, having as an active component from about 0.5 to 90% by weight of a compound of claim 1, together with a pharmaceutically acceptable inert carrier.

4. A method for combating and preventing diseases caused by a restriction in cerebral aging processes which comprises administering a daily dose of about 0.1 to 1 mg/kg of body weight with oral administration, or of about 0.01 to 0.3 mg/kg of body weight with intravenous administration, of a compound of claim 1, to a host in need thereof.

5. 1-(2-Acetylaminoethyl)-pyrrole-3-aldehyde.

* * * * *

UNITED STATES PATENT AND TRADEMARK OFFICE
CERTIFICATE OF CORRECTION

PATENT NO. : 5,043,348

DATED : August 27, 1991

INVENTOR(S) : Gerhard Zoller et al.

It is certified that error appears in the above-identified patent and that said Letters Patent is hereby corrected as shown below:

Col. 8, line 5, replace "11" with --14--;

Col. 8, line 30, replace "15" with --15.4--;

Col. 9, line 21, replace "$C_{16}H_{204N2}O_2$" with --$C_{16}H_{20}N_2O_2$--;

In the Claims:

Claim 1, col. 14, line 20, correct "atoms alkoxy" to read --atoms, alkoxy--.

Signed and Sealed this

Twenty-ninth Day of June, 1993

Attest:

MICHAEL K. KIRK

*Attesting Officer*    Acting Commissioner of Patents and Trademarks